United States Patent [19]

Shimizu

[11] Patent Number: 5,085,217
[45] Date of Patent: Feb. 4, 1992

[54] PAD FOR THE LIVING BODY STIMULUS ELECTRODE

[75] Inventor: Chuji Shimizu, Tokyo, Japan
[73] Assignee: Fukuda Denshi Co., Ltd., Tokyo, Japan
[21] Appl. No.: 609,143
[22] Filed: Nov. 6, 1990

Related U.S. Application Data

[63] Continuation of Ser. No. 443,562, Nov. 29, 1989, abandoned, which is a continuation of Ser. No. 265,593, Nov. 1, 1988, abandoned.

[30] Foreign Application Priority Data

Dec. 7, 1987 [JP] Japan .................. 62-185462
Aug. 29, 1988 [JP] Japan .................. 63-112971

[51] Int. Cl.⁵ .................. A61N 1/04; A61B 5/04
[52] U.S. Cl. ...................... 128/640; 128/639; 128/798; 128/802
[58] Field of Search ............. 128/639, 640, 798, 802, 128/803, 800

[56] References Cited

U.S. PATENT DOCUMENTS

| | | | |
|---|---|---|---|
| 4,248,247 | 2/1981 | Ware et al. | 128/802 |
| 4,365,634 | 12/1982 | Bare et al. | 128/640 |
| 4,419,998 | 12/1983 | Heath | 128/639 |
| 4,583,549 | 4/1986 | Manoli | 128/640 |
| 4,643,193 | 2/1987 | DeMarzo | 128/639 |
| 4,706,680 | 11/1987 | Keusch et al. | 128/640 |
| 4,763,660 | 8/1988 | Kroll et al. | 128/640 |
| 4,799,480 | 1/1989 | Abraham et al. | 128/798 |

Primary Examiner—William E. Kamm
Assistant Examiner—Kennedy J. Schaetzle
Attorney, Agent, or Firm—Sughrue, Mion, Zinn, Macpeak & Seas

[57] ABSTRACT

A pad for securing a stimulus electrode plate on a living body, wherein the stimulus electrode plate includes first and second electrode plates positioned close to each other and integrally formed with a low frequency medical treatment apparatus. The pad includes an insulated substrate sheet which has a profiled portion and a grip projecting outwardly from the profiled portion. The profile portion has a front side confronting a living body and a rear side confronting the stimulus electrode plate. The sheet also includes first and second portions with a center portion defined therebetween. The pad also includes a first pad disposed on the first portion, wherein the first pad has first and second gelhydrate layers. The first gelhydrate layer is positioned at the front side of the first portion, and the second gelhydrate layer is positioned at the rear side of the first portion. The first and second layers are electrically connected to each other, and have conductive and adhesive characteristics. The second pad is disposed on the second portion, wherein the second pad has third and fourth gelhydrate layers. The third gelhydrate layer is positioned at the front side of the second portion, and the fourth gelhydrate layer is positioned at the rear side of the second portion.

7 Claims, 10 Drawing Sheets

Fig. 1

Fig. 2a
FIRST PRIOR ART

Fig. 2b
SECOND PRIOR ART

PAD FOR THE LIVING BODY STIMULUS ELECTRODE

This is a continuation of application Ser. No. 07/443,562 filed on Nov. 29, 1989, now abandoned; which was a Rule 60 continuation application of U.S. application Ser. No. 07/265,593 filed Nov. 1, 1988, also abandoned.

BACKGROUND OF THE INVENTION

1. Field of the Invention

The present invention relates to a pad for use with a living body stimulus electrode. More particularly, it relates to a pad applicable to the living body stimulus electrodes integrated with a low frequency medical treatment apparatus of a coin like disk type.

2. Description of the Related Art

Generally, a living body electrode is defined as a measuring element for measuring electrical phenomenon or as an electric stimulus.

That is to say, the living body electrode is divided into a living body measuring electrode for measuring electric phenomenon emitted from the living body and a living body stimulus electrode for applying electric stimulus to the living body.

For example, the living body measuring electrode is used when electric potentials between two points are emitted from the surface of the living body, and used as input to the electrocardiograph, which produces the electrocardiogram. On the other hand, the living body stimulus electrode is used when the pulse electric current is applied to the living body from the low frequency medical apparatus, in order to ease muscle stiffness or neuralgia.

However, it is undesirable to connect either of the above electrodes directly to the living body, for the following reasons.

(1). An electrode plate, from which the electrode is constructed, is metallic and consequently, the electrode plate cannot easily connect with the living body.

(2) The contact resistance between the skin surface of the living body and the electrode plate, is high and thus it is difficult to measure exactly the electric phenomenon or apply electric stimulus.

(3) The electrode is used by many patients, and dirt or germs attached to their skin adheres to the electrode. Consequently, the electrode would become injurious to their health. Therefore it is an issue of importance that they are not infected by each other.

Figure 1:
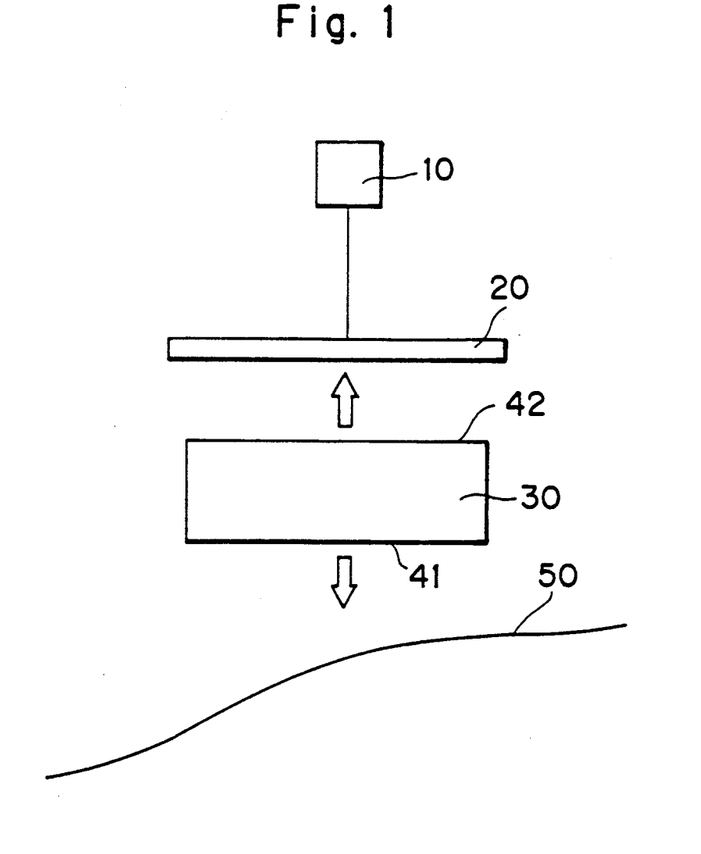
FIG. 1 is a general explanatory drawing of the living body electrode.

Therefore, the living body measuring and stimulus electrodes are both constructed by the electrode plate 20 connected to a medical apparatus 10 of the electrocardiograph or low frequency medical treatment apparatus as well as by a pad 30 connected with the electrode plate 20, as shown in FIG. 1.

The pad 30 is composed of a layer made from conductive and adhesive gelhydrate, and when it is used, one face 42 thereof is adhered to the electrode plate 20, the other face 41 thereof adheres with the skin surface 50 of the living body.

That is to say, the living body electrode is constituted by the pad 30 made of a gelhydrate layer combining conductivity and adhesion. Moreover, the pad 30 is capable of being bonded to or taken off the plate 20.

Accordingly, the defects stated in items (1) to (3) are solved simultaneously.

The pad 30 of the present invention relates to, in particular, a pad for the living body stimulus electrode which is applicable to low frequency medical treatment apparatus of a coin like disk type.

Figure 2A:
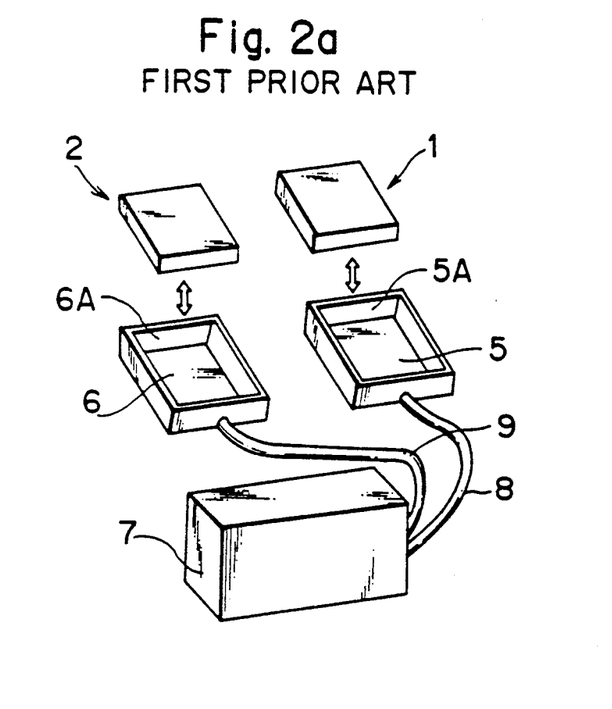
FIG. 2a is an explanatory drawing of a first prior art.

FIG. 2a is an explanatory drawing of a first prior art device.

A low frequency medical treatment apparatus in accordance with FIG. 2a has a first electrode plate 5 and a second electrode plate 6, which are mounted to the top of pad cords 8 and 9 connected with a body 7 and are separate from each other.

A first pad 1 and a second pad 2 are respectively capable of being bonded to or taken off the plates 5 and 6.

When the low frequency medical treatment apparatus is adhesively used, the first and second pads 1 and 2 are respectively applied to the first and second electrode plates 5 and 6, through a first recess 5A and a second recess 6A. Next, the surface of the pads 1 and 2 are contacted closely with, for example, the skin surface of both shoulders of the patient.

However, as electronic parts become smaller, the low frequency medical treatment apparatus composed of them also becomes smaller.

Figure 2B:
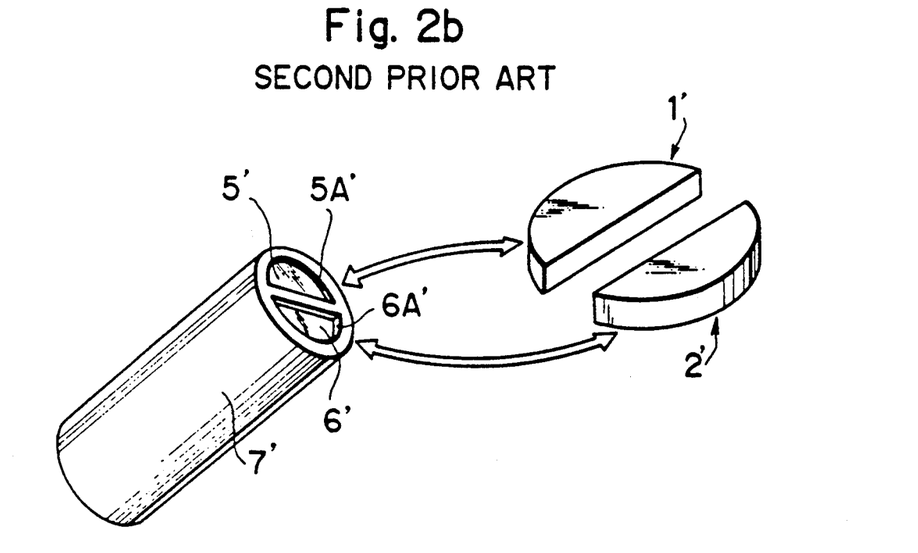
FIG. 2b is an explanatory drawing of a second prior art.

The low frequency medical treatment apparatus of a small size, so-called "coin like disk type", has recently been proposed, as shown in FIG. 2b.

FIG. 2b illustrates a first electrode plate 5' and a second electrode plate 6', which are directly mounted on a body 7'; not through the pad cords 8 and 9 (see FIG. 2a).

In other words, the first and second electrode plates 5' and 6' are integrated with the body 7' and are adjacent to each other. Corresponding first and second pads 1' and 2' are respectively capable of being bonded to or taken off the plates 5' and 6'.

The problems of the second prior art are as follows.

(1) The pads 1' and 2' bonded to or taken off the electrode plates 5' and 6'.

The result is that the above bonding and removal operations must be executed twice, which is very troublesome for the user.

Moreover, since the size of the pads 1' and 2' are each nearly equal to that of corresponding recesses 5A' and 6A', it is very difficult to insert and remove the small pads 1' and 2' into and out of the recesses 5A' and 6A' respectively, by gripping them with the fingers of the user's hand.

It is more difficult for the user to carry out the above operations, because the fingers and the pads become attached firmly to each other as a result of the adhesion characteristics of the pads 1' and 2'.

Consequently, it takes a long time to adhere the pads 1' and 2' to the electrode plates 5' and 6' respectively.

(2) Since the small pads are gripped directly with the fingers, the dirt, for example dust, etc., on the fingers adheres to the whole gelhydrate, and thereby, the pads lose their conductive and adhesive properties.

In particular, when pads 1' and 2' lose their adhesive property, the defect of the second prior art is as follows.

After medical treatment, when the pads 1' and 2' are taken off from the skin surface of the living body together with the body 7' of the medical apparatus, the pads fall off the body 7' and remain stuck to the skin surface, from which the patient feels unpleasantness.

This results from the fact that as the pads lose their adhesion characteristic, they adhere to the skin surface of the living body more than the electrode plate made of metal.

In a word, the second prior art has the problems as follows.

That is to say, even if the pads are intended to be bonded to or taken off of the corresponding electrode plates of the low frequency medical treatment apparatus of a coin like disk type, since the pads are small and separate from each other, it takes a long time to execute the above bonding and removal operations.

Moreover, since the pads do not become attached firmly to the electrode plate, they fall off easily from the above apparatus of a coin like disk type.

SUMMARY OF THE INVENTION

An object of the present invention is to easily and rapidly execute the bonding and removal operations of the pads for the living body stimulus electrode of a low frequency medical treatment apparatus.

Another object of the present invention is to prevent those pads from falling off the same apparatus.

The above-mentioned first object can be achieved by using a pad which comprises a first pad composed of a living body side first gelhydrate layer and an electrode side second gelhydrate layer, having both conductivity and adhesion properties, which are in complementary registration with one side portion of an insulated substrate sheet and are connected to each other, and a second pad composed of a living body side third gelhydrate layer and an electrode side fourth gelhydrate layer, having both conductivity and adhesion properties which are in complementary registration with the other side of said insulated substrate sheet and which are connected to each other, wherein said first and second pads correspond respectively to the first and second electrode plates and are adjacently integrated with the body of the low frequency medical treatment apparatus of a coin like disk type, a center portion of said sheet exposed continuously and wholly, between said first and second pads, and a grip projecting towards and outside of said first and second pads.

The above-mentioned second object can be achieved by a pad for use with the living body stimulus electrode, comprising, a first pad composed of a living body side first gelhydrate layer and an electrode side second gelhydrate layer, having both conductivity and adhesion properties, which are in complementary registration with one side portion of an insulated substrate sheet and are connected to each other, and a second pad composed of a living body side third gelhydrate layer and an electrode side fourth gelhydrate layer, having both conductivity and adhesion properties, which are in complementary registration with the other side portion of said insulated substrate sheet and are connected to each other, wherein said first and second pads correspond respectively to the first and second electrode plates and are adjacently integrated with the body of the low frequency medical treatment apparatus of a coin like disk type, a center portion of said sheet exposed continuously and wholly, between said first and second pads, a bonding layer disposed at least partially on one side surface of a surrounding edge portion of said sheet, which portion projects towards said center portion as well as said first and second pads, said bonding layer capable of bonding to said body.

BRIEF DESCRIPTION OF THE DRAWINGS

Further features and advantages of the present invention will be apparent from the description of the reference to the accompanying drawings, wherein.

DESCRIPTION OF THE PREFERRED EMBODIMENTS (1) First embodiment of the present invention.

Figure 4A:
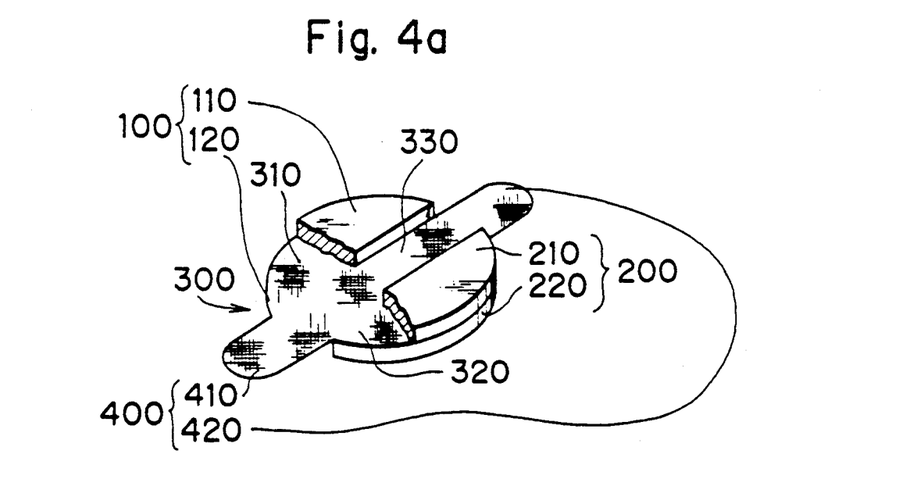
FIG. 4a is a perspective drawing of the first embodiment of the first present invention.
Figure 4B:
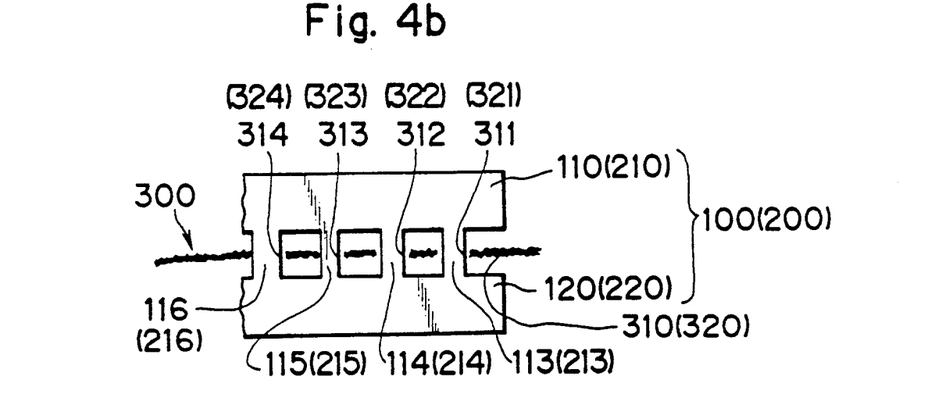
FIG. 4b is a drawing of the relationship between the living body side gelhydrate layer and the electrode side gelhydrate layer of the first embodiment of the present invention.
Figure 4C:
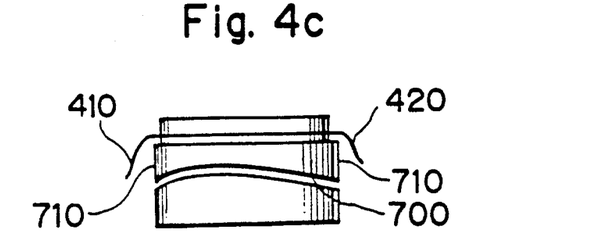
FIG. 4c is a drawing of the grip of the first embodiment of the present invention.

FIGS. 4a, 4b and 4c are drawings of the first embodiment of the first present invention.

FIG. 4a illustrates a first pad 100, shows a second pad 200 and an insulated substrate sheet 300.

Figure 3:
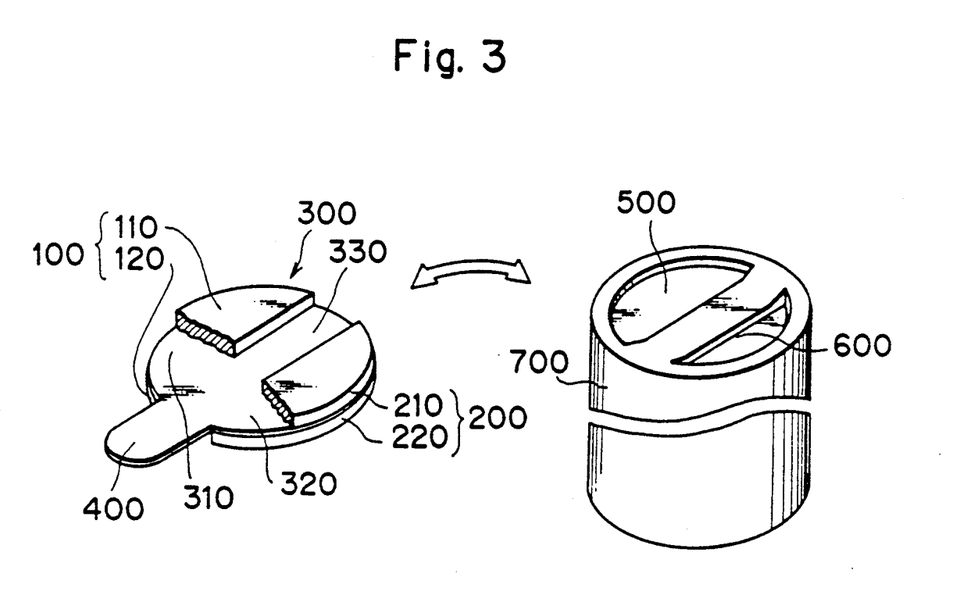
FIG. 3 is a drawing of the first embodiment of the present invention.

The first and second pads 100 and 200 respectively correspond to first and second electrode plates 500 and 600 (see FIG. 3), which are integrated with the body 700 of the low frequency medical treatment apparatus in coin like disk type and are adjacent to each other.

The electrode plates 500 and 600 are respectively formed as semicircles in the first embodiment and thus, the pads 100 and 200 are each formed as low profile semicircles.

The insulated substrate sheet 300 is made of a perforated member, for example textile, knit, nonwoven fabric, etc., and is formed as a disk.

The first pad 100 is composed of a living body side gelhydrate layer 110 and an electrode side gelhydrate layer 120.

The layers 110 and 120 are conductive and adhesive, and they are in complementary registration with one side portion 310 of the sheet 300.

Accordingly, the first pad 100 has a two layer structure.

The living body side and electrode side gelhydrate layers 110 and 120 are capable of being bonded to the skin surface of the living body, and the surface of the electrode plate respectively.

Both layers 110 and 120 are connected to each other by first gelhydrate columns 113-116 (see FIG. 4b), which run through holes 311-314. These holes 311-314 constitute perforations formed at a first portion 310 of the sheet 300 of material, for example, a knit member, the openings through which allow the gelhydrate to pass through from one side to the other.

Thus, the layers 110 and 120 are electrically connected via columns 113-116.

The second pad 200 has also the same constitution as the first pad 100, as is apparent from FIGS. 4a and 4b, which show columns 213-216 and holes 321-324 and only differs from the first pad 100 in being in complementary registration with the other side portion 320.

A center portion 330 of the sheet 300 is exposed continuously and wholly, between pads 100 and 200.

That is to say, since both pads 100 and 200 are opposed to each other through the exposed center portion 330, they are linked and insulated completely from one another.

Both ends of the exposed center portion 330 project towards the outside of the pads 100 and 200, which ends are respectively a first grip 410 and a second grip 420.

Thus, a grip 400 is formed by the first and second grips 410 and 420.

After the pads 100 and 200 are positioned in the body 700 of the low frequency medical treatment apparatus of a coin like disk type, the grips 410 and 420 are bent into contact with the body 700. The grips are capable of being bonded to the outside 710 of the body 700.

Accordingly, there is the effect that the pads 100 and 200 contact closely with the skin surface of the living body, together with the body 700.

In other words, the pads 100 and 200 are prevented from falling off the body 700.

Figure 5A:
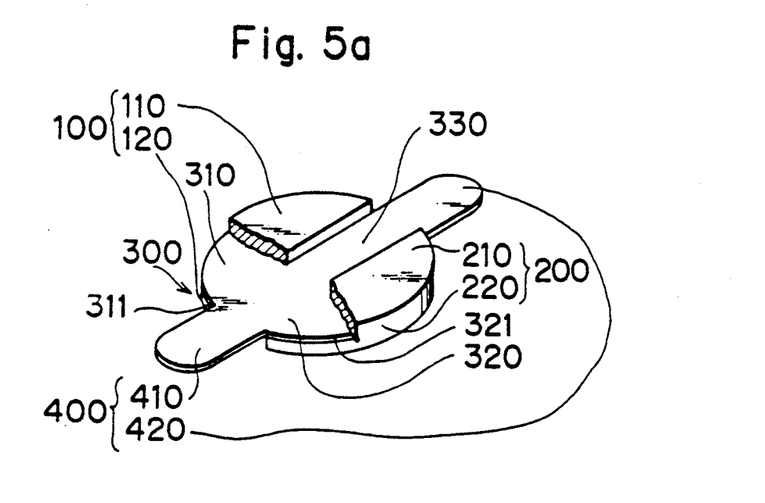
FIG. 5a is a perspective drawing of the second embodiment of the present invention.
Figure 5B:
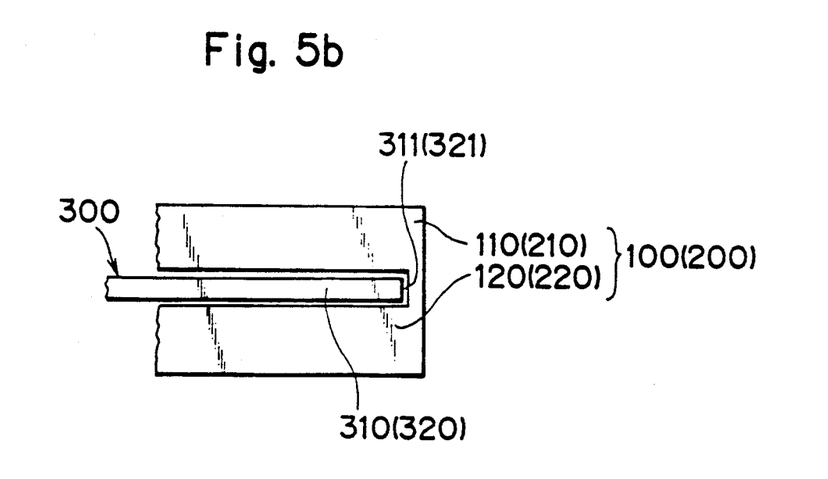
FIG. 5b is a drawing of the relationship between the living body side gelhydrate layer and the electrode side gelhydrate layer of the second embodiment of the present invention.

FIGS. 5a and 5b are drawings of the first embodiment of the present invention with a modification.

The modified first embodiment differs from the first embodiment (see FIGS. 4a, 4b and 4c), in the member constituting the insulated substrate sheet 300 and in means for connecting electrically the living body side gelhydrate layer with the electrode side gelhydrate layer.

That is to say, in the modified first embodiment, the sheet 300 is made of a non-perforated member, for example, rubber, plastic, etc.

Accordingly, the layers 110 and 120 are connected to each other electrically along the end face 311 of one side portion 310 in the sheet 300.

With respect to the layers 210 and 220, they have also the same means for connecting as the layers 110 and 120 (see FIGS. 5a and 5b).

Figure 6:
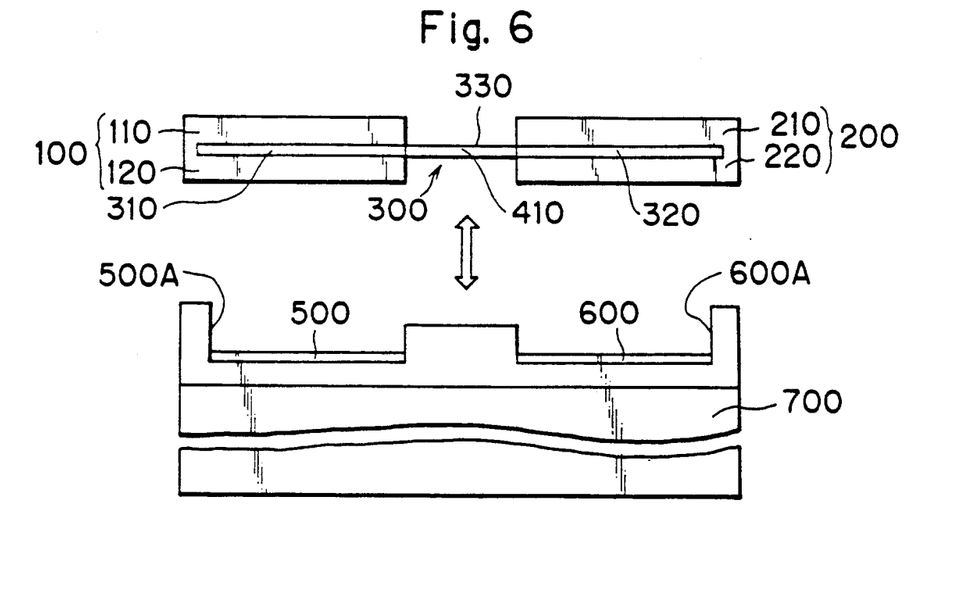
FIG. 6 is an explanatory drawing of the operation of the second embodiment of the present invention.

The operation will be described hereinafter with reference to FIG. 6.

First the layers 120 and 220 are placed into the recesses 500A and 600A of the body 700 while holding the grips 410 and 420 respectively to the electrode plates 500 and 600 in the recesses 500A and 600A by pulling grip 410 in a direction toward the body.

Thereby, both pads 100 and 200, are out of direct contact with the fingers and simultaneously, are capable of being bonded to both electrode plates 500 and 600.

Moreover, the grips 410 and 420 are bent, and are capable of being bonded to the outside 710 of the body 700, for example, by adhesive tape as mentioned before (see FIG. 4c).

After that, the layers 110 and 210 exposed out of the recesses 500A and 600A are made to contact closely with the skin surface of the hand or leg, etc., while holding the body 700 with the pads 100 and 200.

Thereby, since the pads and the body 700 closely contact and adhere to the living body, they do not fall off during medical treatment.

After treatment, the layers 110 and 210 are taken off, together with the body 700, from the skin surface and the grips 410 and 420 are then returned, being taken off from the outside 710.

The layers 120 and 220 are taken off from the corresponding electrode plates 500 and 600, by holding the grip 410 with two fingers, and pulling on the grip 410, thereby pulling pads 120 and 220 out of body plates 500 and 600.

Thereby, both pads 100 and 200 are also, simultaneously and without direct contact with the fingers, capable of being taken off from the electrode plates 500 and 600.

Figure 7:
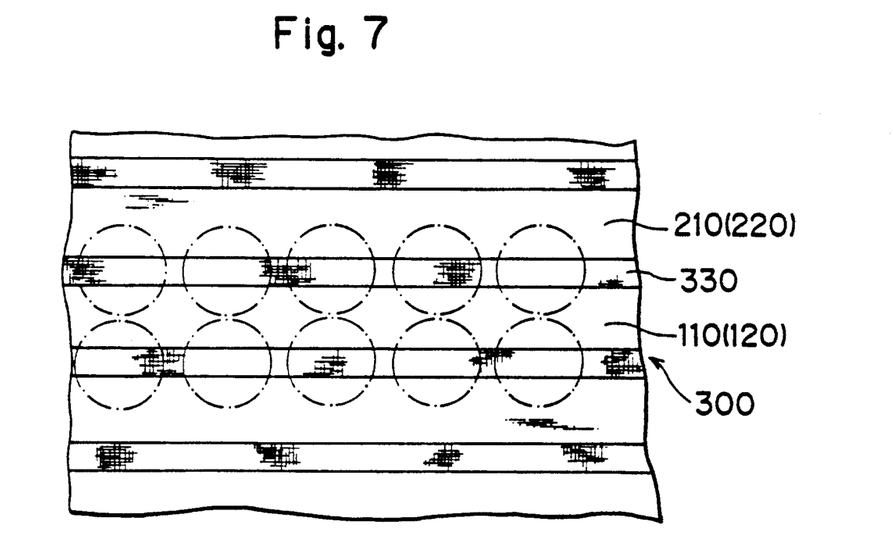
FIG. 7 is a drawing of the method for producing the present invention.

FIG. 7 is a drawing of a method for producing the first embodiment of the present invention.

When a solution, composed of conductive and adhesive acryl gelhydrate, is made to be penetrated from the upper surface of the sheet 300 made of a knit member through holes thereof, it penetrates to the down surface of the sheet 300.

Thereby, when the solution becomes solid by applying ultraviolet rays, the living body side and electrode side gelhydrate layers are formed so as to be in complementary registration with the sheet 300.

Therefore, two gelhydrate layers, which are in complementary registration with the sheet 300, are capable of being disposed in many rows on the opposite sides of the portion where the sheet 300 is exposed as shown in FIG. 7.

Accordingly, many pads of the first embodiment of the present invention are produced by cutting, as shown by chain line of FIG. 7.

(2) The second embodiment of the present invention.

Figure 9A:
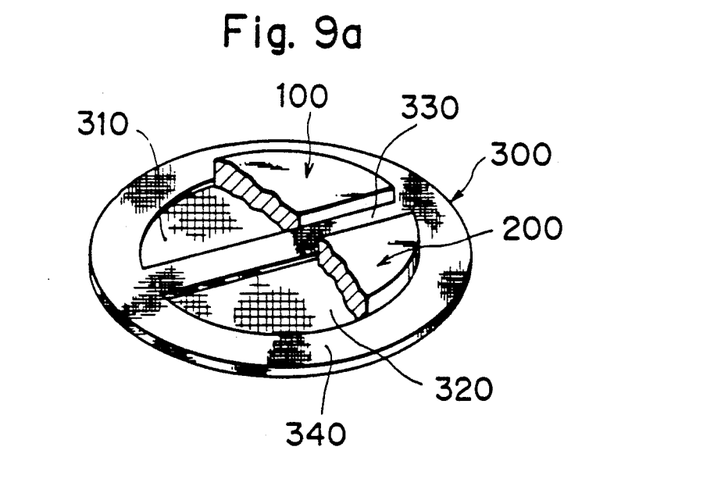
FIG. 9a is a perspective drawing of the front surface of the second embodiment of the present invention.
Figure 9B:
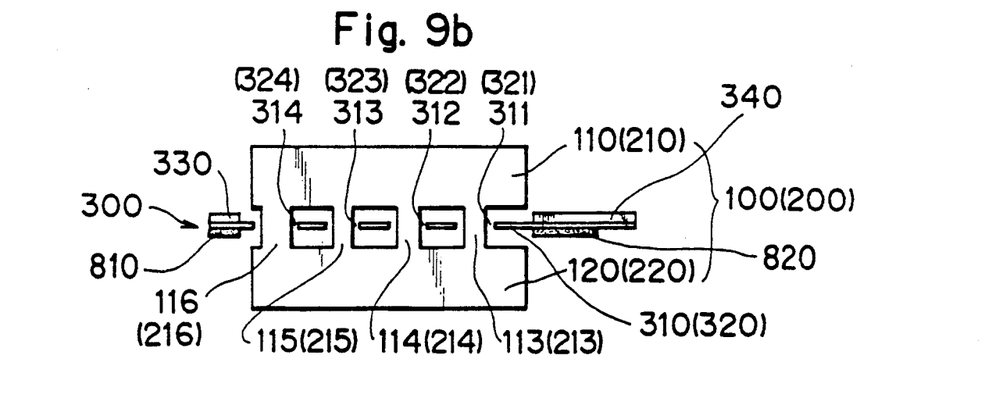
FIG. 9b is a drawing of the relationship between the living body side gelhydrate layer and the electrode side gelhydrate layer of the second embodiment of the present invention.
Figure 9C:
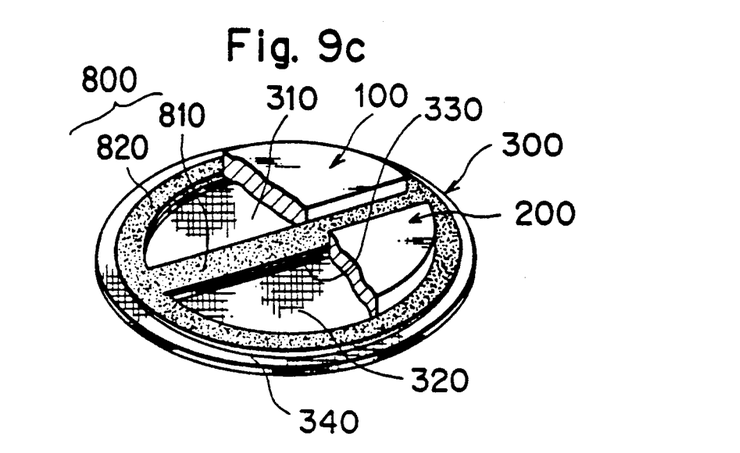
FIG. 9c is a perspective drawing of the back surface of the second embodiment of the present invention.

FIGS. 9a, 9b and 9c are drawings of the second embodiment of the present invention.

FIG. 9a illustrates a first pad 100, a second pad 200, an insulated substrate sheet 300.

Figure 8:
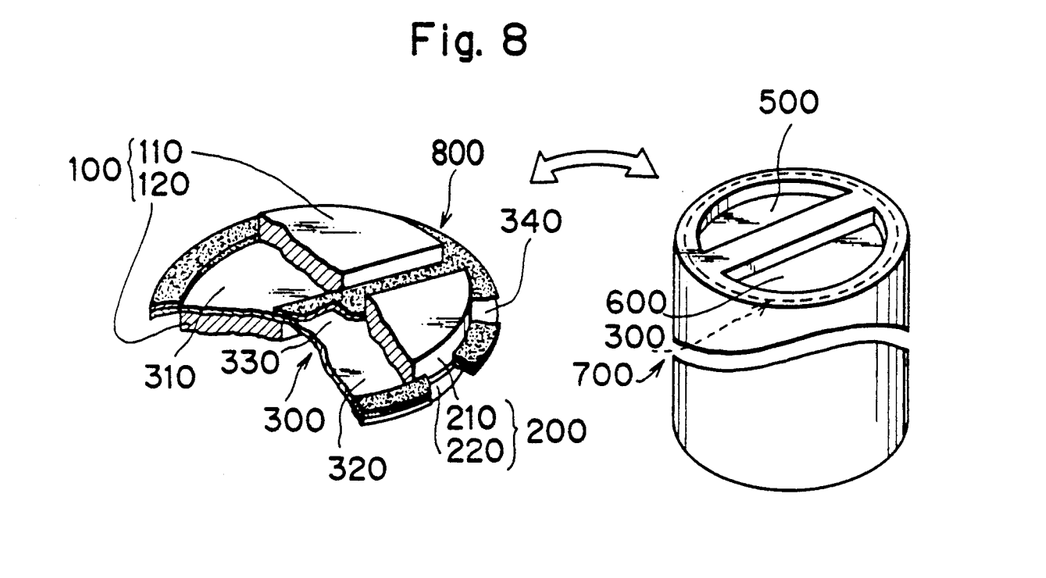
FIG. 8 is a drawing of the principle of the second embodiment of the present invention.

The first and second pads 100 and 200 respectively correspond to first and second electrode plates 500 and 600 (see FIG. 8), which are integrated with the body 700 of the low frequency medical treatment apparatus of a coin like disk type and are adjacent to each other.

Since the electrode plates 500 and 600 are respectively formed as semicircles, the pads 100 and 200 are also each formed as low profile semicircles.

Side portions 310 and 320 of the sheet 300 are made of an absorbent member, for example, cuprammonium rayon nonwoven fabric.

A center portion 330 of the sheet 300 is formed by applying a repellent member, for example a mixture of self linking acryl and titanium oxide, upon the cuprammonium rayon nonwoven fabric (see FIG. 9a).

A surrounding edge portion 340 of the sheet 300 is formed by applying a bonding layer 800 for example acryl bonding agent, upon the back surface of the cuprammonium rayon nonwoven fabric (see FIG. 9c).

The bonding layer 800 may be disposed wholly on the back surfaces of the center and surrounding edge portions 330 and 340.

Alternatively, the bonding layer 800 may be arranged on the whole portion 810 and on the partial portion 820 positioned respectively on the back surfaces of the center and surrounding edge portions 330 and 340, as shown in FIG. 9c.

The first pad 100 is composed of a living body side gelhydrate layer 110 and an electrode side gelhydrate layer 120.

The layers 110 and 120 are both conductive and adhesive, and they are in complementary registration with one side portion 310 of the sheet 300.

Accordingly, the first pad 100 has a two layer structure.

The living body side gelhydrate layer 110 is capable of bonding to the skin surface of the living body, and the electrode side gelhydrate layer 120 bonds to the surface of the electrode plate.

Both layers 110 and 120 are connected to each other by first gelhydrate columns 113-116 (see FIG. 9b), which run through holes 311-314 of one side portion 310 of the sheet 300.

That is to say, the layers 110 and 120 are connected electrically.

The second pad 200 has also the same constitution as the first pad 100, as is apparent from FIGS. 9a and 9b, which show columns 213-216 and holes 321-324, and only differs from the first pad 100 as it is in complementary registration with the other side portion 320.

A center portion 330 of the sheet is exposed continuously and wholly, between these both pads 100 and 200.

That is to say, since both pads 100 and 200 are opposed each other to the exposed center portion 330, they are linked and insulated completely from one another.

Moreover, the surrounding edge portion 340 projects towards the outside of the pads 100 and 200 so as to surround them.

If the pads 100 and 200 are mounted on the body 700 while gripping the surrounding edge portion 340 with fingers, they will, as mentioned later, not fall off the body 700 of the medical apparatus owing to the operation of the bonding layer 800.

In other words, there is the effect to prevent the pads from falling off the low frequency medical treatment apparatus of a coin like disk type.

Figure 10:
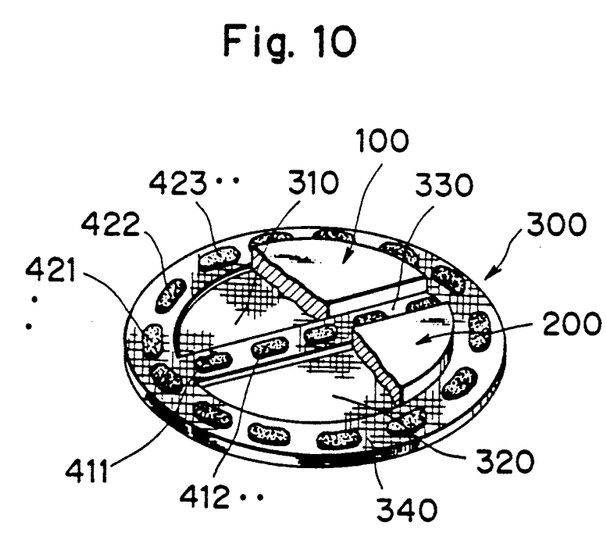
FIG. 10 is a perspective drawing of a modification of the second embodiment of the present invention.

FIG. 10 is a drawing of a modified form of the second embodiment of the present invention.

The modified second embodiment differs (see FIGS. 9a, 9b and 9c) in mode of disposition of the bonding layer on the back surfaces of the center and surrounding edge portions 330 and 340.

That is to say, the bonding layer of the modified second embodiment is disposed partially on the center and surrounding edge portions 330 and 340. This layer consists of a plurality of bonding layers such as 411, 412 and 421-423 placed at regular intervals.

Since the other elements of the modified second embodiment are completely equal to those of the second embodiment, explanation thereof will be omitted.

Figure 11:
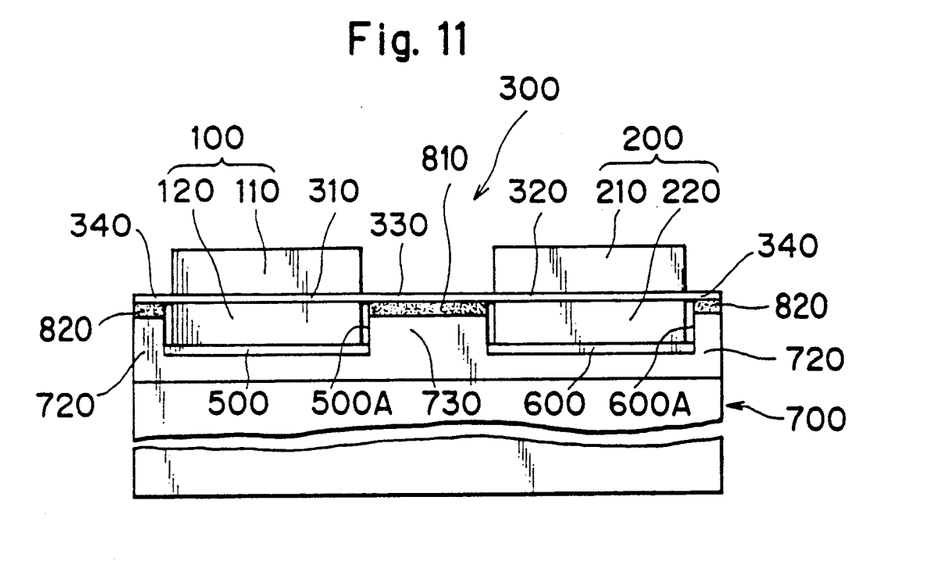
FIG. 11 is an explanatory drawing of the operation of the modified second embodiment; and, FIG. 12 is a drawing of the method for producing the second embodiment of the present invention.

The operation of the modified second embodiment will be described hereinafter with reference to FIG. 11.

At first, after the layers 120 and 220 are turned downward while pinching the surrounding edge portion 340 with two fingers of the hand, they are bonded respectively to the electrode plates 500 and 600 in the recesses 500A and 600A of the body 700. This bonding is achieved by the bonding layers 810 and 820 which correspond to center and surrounding edge portions 730 and 720 of the body 700.

Thereby both pads 100 and 200, are capable of being simultaneously bonded to both electrode plates 500 and 600 as well as the center and surrounding edge portions 730 and 720, without directly contacting the user's fingers.

After that, the layers 110 and 210 exposed out of the recesses 550A and 600A are made to contact closely with the skin surface of the hand or leg etc., by holding the body 700 with the pads 100 and 200.

Thereby, both pads and the body 700 closely contact the living body.

After treatment, the layers 110 and 210 are taken off together with the body 700, from the skin surface. In this case, since the bonding layers 810 and 820, according to the second embodiment of the present invention, is disposed, the pads 100 and 200 do not fall off from the body 700 of the medical apparatus.

The gelhydrate layers 120 and 220, the bonding layer 810, and the bonding layer 820 are taken off respectively, from the corresponding electrode plates 500 and 600, the corresponding center portion 730, and the corresponding surrounding edge portion 720, while pinching again the surrounding edge portion 340 with two fingers of the hand.

Thereby both pads 100 and 200 are capable of simultaneously being taken off the electrode plates 500 and 600, without direct contact with the finger.

Figure 12:
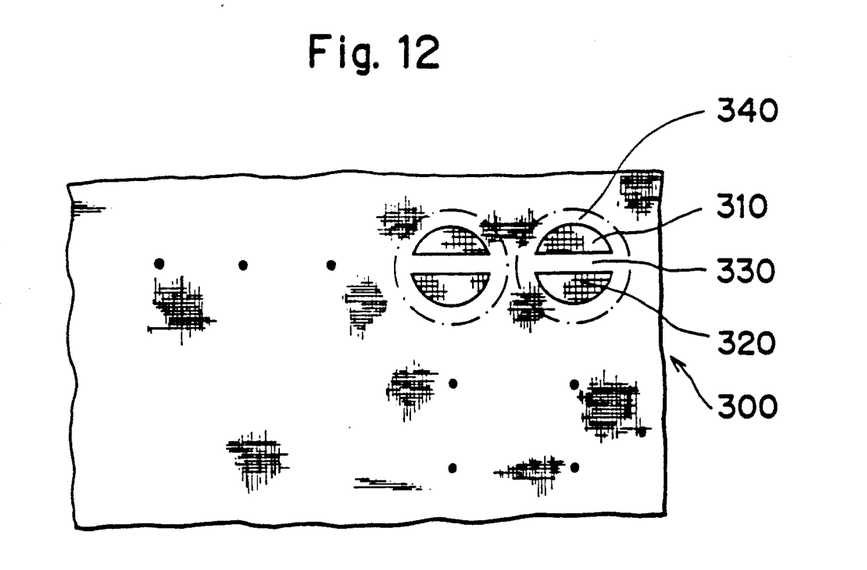

FIG. 12 is a drawing of method for producing the second embodiment of the present invention.

A repellent member, for example a mixture of self linking acryl and titanium oxide, in which openings are formed on the region corresponding to one and the other side portions 310 and 320, is applied upon the upper surface of the sheet 300 made of an absorbent member, for example cuprammonium rayon nonwoven fabric.

On the other hand, adhesive agent and acryl is applied to the down surface of the sheet 300, except for those openings.

Accordingly, the bonding layers are disposed on the down surface of the center and surrounding edge portions 330 and 340 of the sheet 300.

After that, a solution, composed of conductive and adhesive acryl gelhydrate, penetrates the upper surface of the sheet 300 towards those openings.

Since the portions 310 and 320 within those openings are made of an absorbent member, the solution runs through only these portions and is repelled from the center and surrounding edge portions 330 and 340 made respectively of repellent member.

Thereby, the solution also appears on the down surface of the portions 310 and 320.

Consequently, when the solution becomes solid by applying ultraviolet rays, the living body and electrode side gelhydrate layers are formed so as to be in complimentary registration with the sheet 300.

After the above processes, when the sheet 300 is cut as shown by the dotted line of FIG. 12, many pads of the modified second embodiment are produced.

According to the first embodiment of the present invention, since the first and second pads are linked to each other while insulated completely, when the grip is held by the fingers, these two pads are, simultaneously and out of direct contact with the hand, capable of being bonded to and removed from the body of the low frequency medical treatment apparatus of a coin like disk type.

Thereby, the first embodiment of the present invention has the effect that the pad for use with the living body stimulus electrode is easily and rapidly bonded to and taken off the body of the low frequency medical treatment apparatus of a coin like disk type.

According to the second embodiment of the present invention, since the bonding layer 800 is disposed to the pads, adding to the elements of the first embodiment, it is capable of being firmly bonded to the corresponding center and surrounding edge portions 730 and 720 of the body 70.

Thereby, the second embodiment has, adding to the above effect of the first embodiment, the effect that the pad for using with the living body stimulus electrode is prevented from falling off the body of the low frequency medical treatment apparatus of a coin like disk type.

I claim:

1. A pad for securing a stimulus electrode plate on a living body, the stimulus electrode plate being provided with first and second electrode plates positioned close to each other and integral with a body of a low frequency medical treatment apparatus, the pad comprising:

an insulated substrate sheet having a profiled portion and provided with a grip projecting outwardly from the profiled portion, said profiled portion having a front side confronting the living body and a rear side confronting the stimulus electrode plate, said profiled portion having a first portion, a second portion and a center portion defined between the first and second portions;

a first pad disposed on said first portion, said first pad having a first gelhydrate layer and a second gelhydrate layer, said first gelhydrate layer being positioned on said front side of said first portion, and said second gelhydrate layer being positioned on said rear side of said first portion, said first and second gelhydrate layers being electrically connected to each other, and having conductive and adhesive characteristics; and a second pad disposed on said second portion, said second pad having a third gelhydrate layer and a fourth gelhydrate layer, said third gelhydrate layer being positioned on said front side of said second portion, and said fourth gelhydrate layer being positioned on said rear side of said second portion, said third and fourth gelhydrate layers being electrically connected to each other, and having conductive and adhesive characteristics; and said second and fourth gelhydrate layers being adhesively mountable on the first and second electrode plates, respectively.

2. The pad of claim 1, wherein said grip comprises flexible first and second grips for bonding to said body of said treatment apparatus.

3. A pad for securing a stimulus electrode plate on a living body, the stimulus electrode plate being provided with first and second electrode plates positioned close to each other and integral with a body of a low frequency medical treatment apparatus, the pad comprising;

an insulating substrate sheet having a front side confronting a living body and a rear side confronting the stimulus electrode plate, and provided with a first portion, a second portion, a center portion defined between the first and second portions and a surrounding edge portion projecting outwardly for the first, second and center portions;

a first pad disposed on said first portion, said first pad having a first gelhydrate layer and a second gelhydrate layer, said first gelhydrate layer being positioned on said front side of said first portion, and said second gelhydrate layer being positioned on said rear side of said first portion, said first and second gelhydrate layers being electrically connected to each other, and having conductivity and adhesive characteristics; and a second pad disposed on said second portion, said second pad having a third gelhydrate layer and a fourth gelhydrate layer, said third gelhydrate layer being positioned at said front side of said second portion, and said fourth gelhydrate layer, being positioned on said rear side of said second portion, said third and fourth gelhydrate layers being electrically connected to each other, and having conductive and adhesive characteristics;

said second and fourth gelhydrate layers being adhesively mountable on the first and second electrode plates, respectively; and a bonding layer disposed on said rear side of said surrounding edge portion, said bonding layer being capable of bonding to the body of the treatment apparatus.

4. The pad of claim 3, wherein said first and second portions of said sheet are made of an absorbent member,
   said center portion of said sheet is formed by applying a repellent material upon a front surface of said absorbent member, and
   said surrounding edge portion of said sheet is formed by providing said bonding layer upon a back surface of said absorbent member.

5. The pad of claim 3, wherein said bonding layer is disposed wholly on said center and surrounding edge portions of said sheet.

6. The pad of claim 3, wherein said bonding layer is disposed wholly on said center portion and partially on said surrounding edge portion.

7. The pad of claim 3, wherein said bonding layer is disposed partially on said center and surrounding edge portions.

* * * * *